United States Patent
Aizawa et al.

(10) Patent No.: US 8,172,939 B2
(45) Date of Patent: May 8, 2012

(54) MATERIAL FOR CEMENT, AND CEMENT

(75) Inventors: Mamoru Aizawa, Kanagawa (JP);
Yukiko Horiguchi, Kanagawa (JP)

(73) Assignee: Meiji University, Tokyo (JP)

( * ) Notice: Subject to any disclaimer, the term of this patent is extended or adjusted under 35 U.S.C. 154(b) by 349 days.

(21) Appl. No.: 12/063,220

(22) PCT Filed: Sep. 18, 2007

(86) PCT No.: PCT/JP2007/068031
§ 371 (c)(1),
(2), (4) Date: May 30, 2008

(87) PCT Pub. No.: WO2008/090648
PCT Pub. Date: Jul. 31, 2008

(65) Prior Publication Data
US 2010/0132593 A1    Jun. 3, 2010

(30) Foreign Application Priority Data
Jan. 25, 2007   (JP) ................. 2007-014536

(51) Int. Cl.
*C04B 12/02*    (2006.01)

(52) U.S. Cl. .......... 106/690; 106/691; 106/35; 423/308; 423/309; 423/310

(58) Field of Classification Search ............... 106/35, 106/690, 691; 423/308, 309, 310
See application file for complete search history.

(56) References Cited

FOREIGN PATENT DOCUMENTS

| | | | |
|---|---|---|---|
| JP | 63-159207 | A | 7/1988 |
| JP | 04-209711 | A | 7/1992 |
| JP | 05-229807 | A | 9/1993 |
| JP | 06-107514 | A | 4/1994 |
| JP | 2000-500110 | A | 1/2000 |
| JP | 2005-095346 | A | 4/2005 |
| WO | 97/17285 | A1 | 5/1997 |

OTHER PUBLICATIONS

JP 02005095346 A (Aizawa) Apr. 14, 2005. abstract only.*
Takafumi Kanazawa, Rin (Phosphorus), 1997, pp. 65-86, Kenseisha.
The Chemical Society of Japan (ed.): "Kagaku Binran Oyokagakuhen II (Manual of Chemistry, Applied Chemistry Section II), 6th edition", 2003, p. 1485, Maruzen.

* cited by examiner

*Primary Examiner* — Paul Marcantoni
(74) *Attorney, Agent, or Firm* — Sughrue Mion, PLLC

(57) ABSTRACT

A material for cement which comprises a calcium salt powder with an inositol phosphate and/or a salt thereof as adsorbed on the surface thereof, the powder having a specific surface area of 60-120 $m^2/g$. A method of producing a material for cement comprises the step of mixing a calcium ion-containing solution adjusted to alkalinity with a phosphate ion-containing solution to produce a precipitate, the step of maturing the precipitate-containing system while maintaining the alkalinity to obtain a calcium salt powder, the step of recovering the calcium salt powder and drying the same, and the step of immersing the dried calcium salt powder in a solution containing an inositol phosphate and/or a salt thereof to cause the inositol phosphate and/or salt thereof to be adsorbed on the surface of the calcium salt powder.

12 Claims, 3 Drawing Sheets

MATERIAL FOR CEMENT, AND CEMENT

TECHNICAL FIELD

The present invention relates to a material for cement and to a cement.

BACKGROUND ART

Calcium phosphates form a group of biocompatible and biologically active materials almost identical in composition and structure to inorganic substances occurring in vertebrate hard tissues such as bones and teeth.

Among them, hydroxyapatite has properties such that even when implanted in living organisms, it will not cause any rejection reaction or necrosis of the organisms but can readily be assimilated into or directly bound to biological hard tissues; therefore, it is expected to serve as a material for repairing bone defects and bone cavities. While the material forms of hydroxyapatite include compact, porous, granular and cement-like forms, among others, apatite cement which can be molded into any arbitrary shapes is a material having great possibilities in the future.

However, the conventional apatite cements require a long period for hardening and it is also known that the ossification induction period from implantation into living bodies to initiation of assimilation into and conjugation with biological hard tissues is as long as 4 to 5 weeks. This characteristic is associated with patient's pain and is regarded as one of the disadvantages of the currently available apatite cement (Patent Document 1). Further, the conventional apatite cements have a drawback in that they are weak in bending strength (Non-Patent Document 1). A further problem with the conventional apatite cement is that acid-base reactions occur on the occasion of hardening and result in local pH changes until the time of hardening in vivo, inducing inflammatory responses.

Porous bodies comprising β-tricalcium phosphate are currently used as filling materials for transplant bone collection sites or after tumor excision. However, the technology of applying them to wide-ranging defects in long tubular bones supporting a heavy load such as femurs, tibias and the like has not been established as yet. This is because a bone-binding ability sufficient for enduring the excessive stress generated on the interface between a loaded long tubular bone and an artificial bone cannot be obtained in a short period of time. Porous bodies comprising β-tricalcium phosphate are gradually substituted by biological bone but the time required therefor is long; therefore, in real therapy, it is difficult to apply it to loaded parts or sites without using any other fixing material (Non-Patent Document 2). Since β-tricalcium phosphate can characteristically be substituted by biological bone, the development of a material for cement comprising β-tricalcium phosphate is demanded from the clinical side. However, any bioabsorbable cement based on β-tricalcium phosphate alone has not been developed as yet.

One of the present inventors has previously proposed "a chelation-hardening type cement for bone restoration" for solving the problems mentioned above, namely a cement in which the chelation hardening ability of an inositol phosphate is utilized and which comprises one single component capable of hardening without causing changes in pH on the occasion of hardening (Patent Document 2). Inositol phosphates occur in vivo in animals and plants and are very highly safe substances and further are comparable in chelating ability to EDTA.

This cement is expected to be widely applicable as an injectable bone filling material in the fields of orthopedics and dentistry. Since, however, the compression strength provided thereby is 6 to 7 MPa and therefore there is room for investigation from the mechanical strength viewpoint, there is still a problem about the application thereof to sites required to support a high load of at least 14 MPa (e.g. in the case of spinal column compression fracture).

(Patent Document 1) Japanese Patent Laid-Open Publication No. Hei 5-229807.
(Patent Document 2) Japanese Patent Laid-Open Publication No. 2005-95346.
(Non-Patent Document 1) Takafumi Kanazawa: "Rin (Phosphorus)", pages 65-86 (Kenseisha, 1997).
(Non-Patent Document 2) The Chemical Society of Japan (ed.): "Kagaku Binran Oyokagakuhen II (Manual of Chemistry, Applied Chemistry Section II), 6th edition", page 1485 (Maruzen, 2003).

DISCLOSURE OF INVENTION

Problems to be Solved by the Invention

It is an object of the present invention to provide a material for cement and a cement which can harden without accompanying pH changes on the occasion of hardening, having good biocompatibility and a compression strength not lower than 14 MPa which can be applied to sites to support a high load (e.g. in the case of spinal column compression fracture).

Means for Solving the Problems

The above object of the present invention has been accomplished by the following means.

<1> A material for cement, characterized in that it comprises a calcium salt powder with an inositol phosphate and/or a salt thereof as adsorbed on the surface thereof and that the powder has a specific surface area of 60-120 $m^2/g$.

<2> The material for cement according to <1>, wherein the inositol phosphate is phytic acid (inositol hexaphosphate).

<3> The material for cement according to <1> or <2>, wherein the calcium salt is a calcium phosphate.

<4> The material for cement according to <3>, wherein the calcium phosphate is hydroxyapatite.

<5> The material for cement according to <4>, wherein the hydroxyapatite powder shows a (002) plane half width of 0.30-0.45° as determined by X ray diffractometry.

<6> The material for cement according to any of <1> to <5>, wherein the powder has a median diameter within the range of 5-20 μm and the content of particles having a diameter of 3-50 μm is not lower than 60% by volume of the whole powder.

<7> A method of producing the material for cement according to any of <1> to <6>, characterized in that it comprises the step of mixing a calcium ion-containing solution adjusted to alkalinity with a phosphate ion-containing solution to produce a precipitate, the step of maturing the precipitate-containing system while maintaining the alkalinity to obtain a calcium salt powder, the step of recovering the calcium salt powder and drying the same, and the step of immersing the dried calcium salt powder in a solution containing an inositol phosphate and/or a salt thereof to cause the inositol phosphate and/or salt thereof to be adsorbed on the surface of the calcium salt powder.

<8> The method of producing the material for cement according to <7>, wherein the precipitate-containing system is maintained at a temperature of 20-70° C. to obtain a powder.

<9> The method of producing the material for cement according to <7> or <8>, wherein the step of recovering and drying the calcium salt powder is carried out in the manner of freeze drying or drying with heating at 50-150° C.

<10> The method of producing the material for cement according to any of <7> to <9> which further comprises the step of pulverizing the dried calcium salt powder.

<11> The method of producing the material for cement according to <10>, wherein the step of pulverizing is carried out in the manner of wet pulverization using a vessel-driven medium mill.

<12> The method of producing the material for cement according to any of <1> to <6>, characterized in that it comprises the step of mixing a calcium ion-containing solution adjusted to alkalinity, a phosphate ion-containing solution and a solution containing an inositol phosphate and/or a salt thereof together to produce a precipitate, and the step of maturing the precipitate-containing system while maintaining the alkalinity to obtain a inositol phosphate-carrying calcium salt powder.

<13> A cement characterized in that it is produced by kneading at least one material for cement selected from the group consisting of the materials for cement according to <1> to <6> and the materials for cement obtained by the methods of producing the material for cement according to <7> to <12> with an aqueous solvent, followed by hardening.

<14> The cement according to <13> which has a compression strength, after hardening, of not lower than 14 MPa.

EFFECTS OF THE INVENTION

The material for cement according to the present invention hardens without accompanying pH changes and provides a cement having biocompatibility and a compression strength of 14 MPa or higher capable of being applied to highly loaded sites (e.g. in the case of spinal column compression fracture). The cement according to the present invention is used for filling bone defects or cavities to facilitate new bone development and is readily integrated with hard tissues in vivo.

BEST MODE FOR CARRYING OUT THE INVENTION

Figure 1:
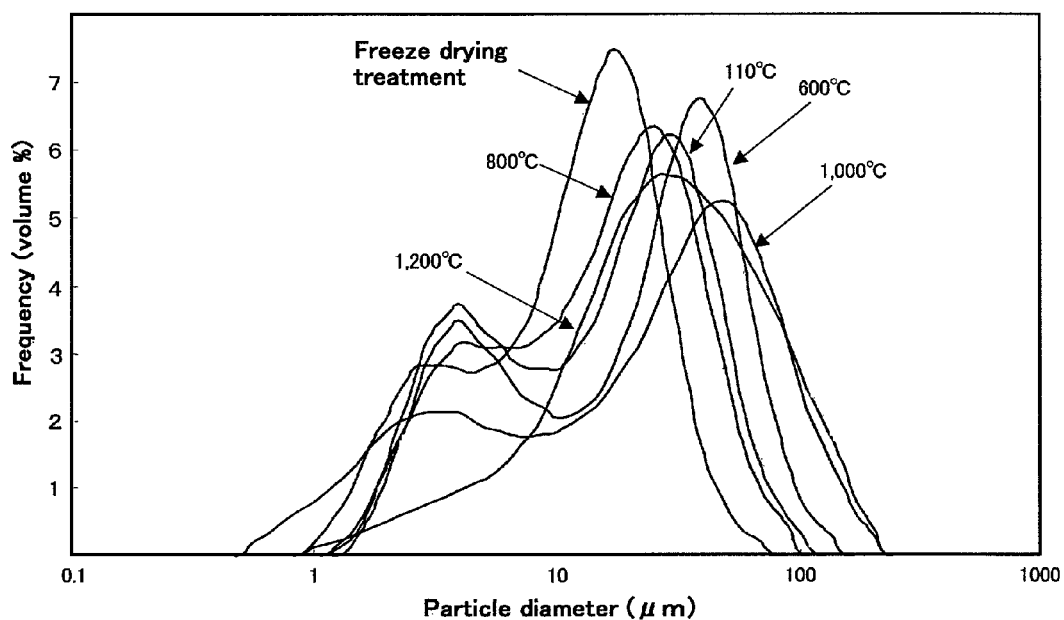
FIG. 1 shows the results of particle size distribution measurements of a wet-synthesized HAp/IP$_6$ powder, a HAp/IP$_6$ powder dried at 110° C., and a calcined HAp/IP$_6$ powder.

The material for cement according to the present invention is characterized in that it comprises a calcium salt powder with an inositol phosphate and/or a salt thereof as adsorbed on the surface thereof and that the powder has a specific surface area of 60-120 m$^2$/g.

In the following, the material for cement according to the present invention is described.

<Inositol Phosphate or a Salt Thereof>

The inositol phosphate to be used in the present invention includes inositol monophosphate, inositol diphosphate, inositol triphosphate, inositol tetraphosphate, inositol pentaphosphate and phytic acid (inositol hexaphosphate).

Preferred as the inositol phosphate salt are alkali metal salts or alkaline earth metal salts, such as sodium, potassium, magnesium, calcium, barium salts and the like.

Among these, phytic acid, sodium phytate and potassium phytate are preferred. When phytic acid is used, the pH is adjusted to 6-11 with sodium hydroxide or potassium hydroxide, and therefore, phytic acid is used substantially in the form of sodium phytate or potassium phytate.

Sodium phytate includes several species differing in the content of water of crystallization, for example sodium phytate 38 hydrate, sodium phytate 47 hydrate and sodium phytate 12 hydrate; all of these can be preferably used.

In the present invention, the method of producing phytic acid (hereinafter also referred to as "IP$_6$") or an alkali metal phytate is not particularly restricted but those phytic acid or alkali metal salt species produced by all available production methods may be used. For example, sodium phytate can be obtained by extracting a defatted plant seed powder with diluted hydrochloric acid, precipitating and purifying phytic acid from the extract in the form of an insoluble copper salt or iron salt, for instance, then converting the same to the sodium salt and precipitating the sodium salt by addition of an alcohol.

<Calcium Salt>

Preferably used as the calcium salt are calcium phosphate, calcium carbonate and the like. These may be used singly or two of them may be used simultaneously. In the case of using one single species, calcium phosphate is preferably used.

Hydroxyapatite, α-tricalcium phosphate, β-tricalcium phosphate, tetracalcium phosphate, octacalcium phosphate, calcium hydrogen phosphate, calcium dihydrogen phosphate and noncrystalline calcium phosphate are preferred as the calcium phosphate, hydroxyapatite, α-tricalcium phosphate and β-tricalcium phosphate are more preferred, and hydroxyapatite is particularly preferred. These may be used singly or two or more species may be used simultaneously.

<Specific Surface Area>

In the present invention, the calcium salt powder carrying the above-mentioned inositol phosphate and/or the salt thereof as adsorbed on the surface thereof has a specific surface area of 60-120 m$^2$/g, preferably 80-120 m$^2$/g, more preferably 100-120 m$^2$/g. When the specific surface area of the powder is smaller than 60 m$^2$/g, the inositol phosphate and/or the salt thereof will not be adsorbed on the surface of the calcium salt powder in a sufficient amount, so that the number of chelating sites will decrease; hence, when used as a material for cement, any cement having a sufficient compression strength cannot be obtained.

The specific surface area (SSA) of the powder can be measured by the BET method using a Micromeritics automated surface area measuring apparatus FlowSorb III 2305 (product of Shimadzu Corporation). Liquefied nitrogen was used as the coolant. The corrected value of the amount at saturated adsorption was calculated using the following formula.

$$SSA = (273.2/\text{atmospheric temperature (° C.)} \times \text{atmospheric pressure (mm Hg)}/760) \times ((6.023 \times 10^{23} \times 16.2 \times 10^{-20})/(22.414 \times 10) \times (1-(\text{nitrogen percentage (\%)} \times \text{atmospheric pressure (mm Hg)})/775)$$

The amount of gas adsorbed on the powder upon cooling of the sample with the coolant (adsorption data) and the amount of gas released from the powder upon taking out of the sample from the coolant (desorption data) were measured. The desorption data was employed as the experimental value.

<Half Width by X Ray Diffractometry>

In the present invention, the half width of the hydroxyapatite powder (002) plane diffraction peak as measured by X ray diffractometry is preferably 0.30-0.45°, more preferably 0.32-0.45°, still more preferably 0.35-0.45°. When the half width is smaller than 0.30°, no sufficient compression strength can be obtained.

The crystallite orientation and crystal structure determination, crystal constituent identification, crystallinity evaluation, and three-dimensional crystallite texture evaluation of hydroxyapatite and the like can be carried out simultaneously by X ray diffractometry.

Among them, the crystallinity evaluation is carried out by measuring the half width of each diffraction peak. The hydroxyapatite powder (002) plane half width can be calculated based on the diffraction peak at a Bragg angle ($2\theta$) of 25.6°. The half width is the width of the diffraction peak at a position where the peak intensity becomes half and is expressed in degrees (angle). An increase in this half width means a decrease in crystallinity. The crystallinity is decided by the crystallite size and lattice strain and, when the crystallites are small and the lattice strain is intense, the crystallinity is low. Therefore, in the present invention, the calcium salt powder is preferably great in the half width and low in crystallinity.

<Method of Producing Calcium Salt Powder>

The method of producing the calcium salt powder to be used in the material for cement according to the present invention is not particularly restricted but the calcium salt powder may be one produced by any of the available methods. As the method of producing the calcium salt powder, there may be mentioned, for example, the dry method, semi-dry method and wet method and, among them, the wet method is preferred. By using the wet method, it is possible to mass-produce a highly pure calcium salt powder having low crystallinity and a large specific surface area.

<Method 1 of Producing a Material for Cement>
<Production of a Calcium Salt Powder by the Wet Method>

The production, by the wet method, of a calcium salt powder to be used in the present invention is now described.

The method of producing the calcium salt powder according to the present invention is characterized in that it comprises the step of mixing a calcium ion-containing solution adjusted to alkalinity with a phosphate ion-containing solution to produce a precipitate (step 1), the step of maturing the precipitate-containing system while maintaining the alkalinity thereof to obtain a calcium salt powder (step 2), and the step of recovering and drying the calcium salt powder (step 3).

The (step 1) and (step 2) are explained.

In the step of mixing a calcium ion-containing solution adjusted to alkalinity with a phosphate ion-containing solution to produce a precipitate (step 1), the method of mixing is not restricted but may use the simultaneous mixing method, the one side mixing method or a combination thereof, for instance.

The simultaneous mixing method comprises pouring a calcium ion-containing solution adjusted to alkalinity and a phosphate ion-containing solution simultaneously into a precipitation vessel for calcium phosphate formation. As an example, mention may be made of the so-called controlled double jet method according to which the ratio between the calcium ion concentration and phosphate ion concentration in the liquid phase in which the calcium salt precipitate is formed is maintained at a constant level.

The one side mixing method comprises adding a phosphate ion (or calcium ion)-containing solution to a solution excess in calcium ion (or excess in phosphate ion) adjusted to alkalinity to form a calcium salt precipitate. The one side mixing method for synthesizing hydroxyapatite as an example of the calcium salt is explained in the following.

A phosphate ion-containing solution is added dropwise to a calcium ion-containing solution, for example a calcium hydroxide solution, adjusted in advance to alkalinity, and the resulting precipitate is matured while the alkalinity thereof is maintained, whereby a hydroxyapatite powder is obtained. Preferably used as the alkaline substance for pH adjustment of the solution is ammonia. The pH of the reaction mixture is preferably 7-12, more preferably 10-11.

The concentration of the calcium ion-containing solution is preferably 0.5-2.0 M, more preferably 0.7-1.5 M, still more preferably 0.9-1.1 M. The concentration of the phosphate ion-containing solution is preferably 0.3-1.2 M, more preferably 0.42-0.9 M, still more preferably 0.54-0.66 M.

When the calcium salt is hydroxyapatite, the ratio between the Ca and P elements contained in the hydroxyapatite powder, namely the Ca/P element ratio, is preferably 1.60-1.70, more preferably 1.63-1.69. The Ca/P element ratio adjustment is carried out by adjusting the concentration ratio between the calcium ion-containing solution and phosphate ion-containing solution. For example, The Ca/P element ratio in the solution can be adjusted to about 1.67 by adjusting the ratio between the molar concentration of the calcium ion-containing solution and the molar concentration of the aqueous phosphoric acid solution to 5:3.

When the Ca/P element ratio is within the above numerical value range, a hydroxyapatite powder can be obtained efficiently. When hydroxyapatite within the above ratio range is used as a material for cement, a cement excellent in compression strength can be obtained.

In the (step 1), the temperature in the reaction vessel is generally 20-70° C., preferably 30-50° C., particularly preferably 30-40° C. Within the above numerical value range, fine apatite crystals with a large specific surface area can be easily prepared.

For avoiding the incorporation of carbon dioxide in the air into the calcium salt powder, the series of procedures are preferably carried out in an inert gas atmosphere, for example in gaseous nitrogen. In this process, the purity of each material used is reflected in the purity of the calcium salt powder obtained. Therefore, when high-purity materials are used, a high-purity calcium salt powder can be obtained.

The step of recovering and drying the calcium salt powder (step 3) is now explained.

The step of recovering and drying the calcium salt powder is preferably carried out in the manner of freeze drying or drying by heating at 50-150° C., more preferably in the manner of freeze drying. Freeze drying can give a calcium salt powder larger in specific surface area.

When freeze drying is employed in the step of recovering and drying the calcium salt powder, the drying temperature is preferably −100 to −50° C., more preferably −90 to −70° C. The drying time is preferably 1-48 hours.

When drying by heating is employed in the step of recovering and drying the calcium salt powder, the drying temperature is preferably 50-150° C., more preferably 70-130° C., still more preferably 90-120° C. The drying time is preferably 1-48 hours.

In the art, organic components, among others, are removed from the calcium salt powder by heat treatment or immersion in an acidic solution, for instance, so that the rejection response from the application target living body may be lessened. In the case of heat treatment, organic components, among others, can be removed by heat treatment at 300-700° C. for 1 to 1,000 hours.

In the art, the calcium salt powder deprived of organic components is calcined at 600-1,400° C. to adjust the crystal diameter, porosity, orientation and mechanical characteristics of the calcium phosphate-based substance.

The calcium salt to be used in the material for cement according to the present invention is free of any substance causing the rejection reaction from the living body. Therefore, the removal of organic components and the like by heat treatment, for instance, is not necessary. Further, a calcium salt powder with a low degree of crystallinity and a large specific surface area can be obtained by freeze drying or drying by heating at 50-150° C., without carrying out the calcination at 600-1,400° C.

<Median Diameter>

The calcium salt powder to be used in the present invention preferably has a median diameter within the range of 3-50 μm, more preferably 5-20 μm. Within the above numerical value range, a powder having a larger specific surface area can be obtained and, therefore, a cement excellent in compression strength can be obtained. The powder median diameter can be calculated using a laser diffraction/scattering particle size distribution measurement apparatus LA-300 (product of Horiba Ltd.), for instance.

<Particle Size Distribution>

As for the particle size distribution in the calcium salt powder, the percentage (% by volume) of particles having a diameter of 3-50 μm is preferably not lower than 60% of the total amount of particles, more preferably not lower than 80% of the total amount of particles.

This percentage can be determined, for example, by plotting the particle diameter-cumulative frequency relationship based on the measurement results obtained using the laser diffraction/scattering particle size distribution measurement apparatus LA-300 (product of Horiba Ltd.) and determining the cumulative frequency for the range of 3-50 μm.

<Pulverizer>

Preferably, the production method further includes the step of mechanically pulverizing the calcium salt powder so that the specific surface area of the calcium salt may be increased in the present invention. Mechanical pulverization not only increases the specific surface area but also can efficiently decrease the crystallinity.

Various pulverizers can be used as the means for mechanically pulverizing the calcium salt powder. Any of the known pulverizers can be used provided that they can adjust the powder specific surface area and particle diameter to the respective desired ranges. Specific examples include, but are not limited to, vertical roller mills, high-speed rotary mills, vessel-driven medium mills, and agitated medium mills; among them, vessel-driven medium mills are preferred.

The vessel-driven medium mills are micropulverizers comprising a generally cylindrical mill vessel containing grinding media such as steel balls, ceramic balls, stone balls, steel rods, pebbles or beads; pulverization is effected by driving the mill vessel. According to the mode of movement of the mills, they are roughly classified into rolling mills, vibrating mills and satellite mills, and satellite mills can be preferably used. According to the kind of grinding media, they are also classified into ball mills, pebble mills and rod mills, for instance, and ball mills are preferred. Therefore, satellite ball mills can be preferably used in the present invention.

Satellite ball mills are of the type such that a cylindrical pulverizing vessel rotates on its axis and at the same time revolves around the central mill axis parallel to the axis of rotation. As specific examples, there may be mentioned satellite ball mills P-4, P-5, P-6 and P-7 (product of Fritsch).

The grinding media to be used in such satellite ball mills are not restricted but may be any conventional ones. As examples, there may be mentioned steel balls (SWRM, $SUJ_2$, SUS 440, chromium steel), ceramic balls (high alumina, steatite, zirconia (zirconium oxide), silicon carbide, silicon nitride), glass balls (ordinary soda glass, alkali-free glass, high B), super hard balls (tungsten carbide), natural stone balls (flint $SiO_2$), and plastic polyamide balls. Among them, zirconia (zirconium oxide) balls can be preferably used.

The grinding media preferably have a Mohs hardness of 8.0-9.0. Within such numerical value range, the media can be used repeatedly without wear or damage. Zirconia has a Mohs hardness of 8.5. The grinding media preferably have a diameter of 10-40 mm, more preferably 10-20 mm.

In the present invention, the pulverization is preferably carried out in the manner of wet pulverization.

Generally, wet pulverization is more suited for the formation of fine powders than dry pulverization. This is presumably due to the synergy between the effect of reducing the particle surface energy (Rehbinder effect) and the effect of suppressing the mutual aggregation of particles and maintaining the material to be pulverized in a dispersed state, each produced by wetting of the particle surface with a liquid. When pulverization is carried out by the dry method, fine particles coat the pulverization media, causing the cushioning phenomenon; the pulverization efficiency is thus reduced.

<Adsorption of an Inositol Phosphate and/or a Salt Thereof>

For causing an inositol phosphate and/or a salt thereof (hereinafter also referred to as "inositol phosphate etc.") to be adsorbed on the surface of the calcium salt powder, the calcium salt powder is immersed in a diluted solution of the inositol phosphate etc. It is considered that the inositol phosphate etc. are chemically adsorbed on the surface of the calcium salt powder.

After mixing the calcium salt power with an aqueous solution of the inositol phosphate etc. for causing the latter to be adsorbed on the powder surface, the powder is separated and dried, whereby a powder resulting from adsorption of the inositol phosphate etc. on the calcium salt powder can be obtained.

When an aqueous solution of the inositol phosphate etc. is used, the aqueous solution is preferably adjusted in advance to pH 6-11, more preferably pH 6-8, by adding an aqueous alkali solution thereto. The aqueous alkali solution to be used for pH adjustment is not particularly restricted but may be an aqueous solution of sodium hydroxide or an aqueous solution of potassium hydroxide, for instance.

The concentration of the aqueous solution of the inositol phosphate etc. is preferably 1,000-10,000 ppm, more preferably 1,000-5,000 ppm, still more preferably 1,000-2,500 ppm.

The mole ratio of the inositol phosphate etc. to the calcium salt is preferably 0.001-0.1, more preferably 0.001-0.05.

The method of causing adsorption is not particularly restricted but the aqueous solution of the inositol phosphate etc. with the calcium salt powder immersed therein is properly stirred or shaken and, after completion of adsorption, the desired powder is separated.

The mixing temperature is preferably 20-60° C., more preferably 20-40° C. The mixing time is preferably 2-24 hours, more preferably 2-10 hours.

The powder with the inositol phosphate etc. adsorbed thereon is preferably dried by freeze drying or by heating at 50-150° C., more preferably by freeze drying, like in the step of recovering and drying the calcium salt powder. The drying time is preferably 12-48 hours, more preferably 12-24 hours.

The material for cement as prepared in the above manner occurs as a powder with the inositol phosphate etc. adsorbed on the surface of the calcium salt powder. In particular, the adsorption of the inositol phosphate etc. on the calcium salt powder can be approximated by monomolecular layer adsorption from the Langmuir adsorption isotherm plot.

<Method 2 of Producing a Material for Cement>

In producing the material for cement, the following method can also be employed.

Specifically, the method that can also be employed is characterized in that it comprises the step of mixing a calcium ion-containing solution adjusted to alkalinity, a phosphate ion-containing solution and a solution containing an inositol phosphate and/or a salt thereof together to produce a precipitate and the step of maturing the precipitate-containing system while maintaining the same at alkalinity to obtain an inositol phosphate-containing calcium salt powder.

Thus, differing from the afore-mentioned production method comprising causing the inositol phosphate etc. to be adsorbed on the calcium salt powder, this method is characterized by simultaneously adding a solution containing the inositol phosphate etc. on the occasion of synthesizing the calcium salt. Like in the case of the afore-mentioned method of producing a material for cement, the method of mixing of the solutions is not restricted but may use any of the one side mixing method, the simultaneous mixing method and a combination thereof, for instance.

<Cement>

The cement according to the present invention is now described.

The material for cement according to the present invention is used in the form of a paste prepared by kneading the same in an aqueous solvent. While water is mainly used as the aqueous solvent, a solvent prepared by adding a water-miscible solvent, such as ethanol, to water can also be used. The kneaded material for cement is used for filling a bone defect site or a like affected part and then allowed to harden to prepare a cement.

As for kneading time, it is preferable that the procedure from kneading to filling be finished in 3 minutes. The pH of the aqueous solvent is preferably 6-11, and water having a pH of 6-8 is more preferred.

The weight ratio between the material for cement and the aqueous medium, namely the solid/liquid ratio (powder/kneading liquid), is generally 1/0.30-1/0.60, preferably 1/0.31-1/0.45, more preferably 1/0.32-1/0.40. Within the above numerical value range, a cement excellent in compression strength can be obtained after hardening.

On the occasion of kneading of the material for cement according to the present invention in an aqueous solvent, there may be added, according to the disease to be treated, one or more of polysaccharides such as starch, glucosaminoglycans, alginic acid, chitin, chitosan and heparin, proteins such as collagen, gelatin and derivatives of these, and physiologically active substances such as antirheumatic therapeutic agents, antiinflammatory agents, antibiotics, antitumor agents, bone inducing factor, retinoic acid and retinoic acid derivatives.

After filling of a bone defect site or a like affected part with the above paste, the hardening begins in 2-3 minutes and is complete in about 10 minutes to give a cement. This cement binds to a newborn bone and integrated with a hard tissue in vivo.

Unlike the conventional apatite cement, the cement according to the present invention does not cause acid-base reactions on the occasion of hardening, hence causing no pH changes before and after hardening. Therefore, the possibility of the cement according to the present invention causing inflammatory responses is much smaller.

The cement according to the present invention which requires a short hardening time can shorten the treatment period and can reduce the pain on the patients' side as well. The cement according to the present invention can be used in the treatment of bone fracture, osteoporosis and chronic rheumatoid arthritis, and the like.

The present inventors have succeeded in increasing the strength of cement samples by comminuting the raw material for cement. The cements so far obtained according to the present invention show a compression strength of about 14-25 MPa and it is now possible to apply them to loaded sites. In particular, it is obvious that the coming of a superannuated society will result in an increasing number of treatments regarding "compression fracture" intrinsic in persons of advanced age; and by injection of the "intensified chelation hardening type cement for bone restoration" provided by the present invention to apply to spinal column compression fracture, it becomes possible to construct a clinically low-invasive (with a reduced burden or influence on the living body) therapeutic method. The construction of such a therapeutic method using this new cement promises improvements in QOL (quality of life) from the global viewpoint.

EXAMPLES

Example 1

Investigations Concerning Synthesis Conditions

For investigating the synthesis conditions, HAp (hydroxyapatite) was synthesized under the experimental conditions shown in Table 1.

The following five experimental parameters were used:
Synthesis temperature (37, 50, 70° C.);
Rate of stirring (200, 400, 800 rpm);
Reagent concentrations (0.1 M calcium hydroxide and 0.06 M phosphoric acid, 0.5 M calcium hydroxide and 0.3 M phosphoric acid, 1.0 M calcium hydroxide and 0.6 M phosphoric acid, 2.0 M calcium hydroxide and 1.2 M phosphoric acid);
pH adjusting agent (25% $NH_4OH$, 1.5 M NaOH, 1.5 M KOH);
Rate of dropping of phosphoric acid (17, 4.2 ml/min).

<HAp Powder Preparation by Wet Synthesis>

The method of synthesis was specifically as follows.

First, 500 $cm^3$ of a calcium hydroxide suspension was prepared and 500 $cm^3$ of an aqueous phosphoric acid solution was added dropwise thereto. The concentrations of calcium hydroxide and phosphoric acid were adjusted so that the Ca/P ratio might amount to 1.67 (molar ratio). The pH in the reaction vessel was adjusted with a pH adjusting agent so that it might be such that 10<pH<11. After completion of the dropping of the aqueous phosphoric acid solution, the whole mixture was further stirred for 1 hour and then allowed to stand in an incubator set at 37° C. for 24 hours for maturation. After maturation, the HAp slurry was recovered by suction filtration and frozen overnight in a freezer at −80° C. The frozen HAp slurry was dried for 24 hours using a freeze dryer Free Zone (trademark) (product of Labconco) to give a wet-synthesized HAp powder.

<Preparation of an Aqueous Solution of Phytic Acid ($IP_6$)>

A 1.00 g portion of 50 weight % $IP_6$ aqueous solution (product of Wako Pure Chemical Industries) was exactly weighed, then diluted to about 300 cm³ with purified water, then adjusted to pH 7.3 with an aqueous solution of sodium hydroxide and then supplemented with purified water to the mark of a 500 cm³ volumetric flask. An aqueous solution of $IP_6$ with a concentration of 1,000 ppm was thus prepared.

<Preparation of a Wet-Synthesized HAp/$IP_6$ Powder by Surface Modification>

A 10.0 g portion of the wet-synthesized HAp powder was suspended in 200 cm³ of the aqueous solution of $IP_6$ with a concentration of 1,000 ppm and the suspension was stirred at 37° C. at a rate of 400 rpm for 5 hours, followed by suction filtration. The slurry obtained was washed with purified water and then frozen overnight at −80° C. The frozen HAp/$IP_6$ slurry was dried using the freeze dryer Free Zone (trademark) (product of Labconco) for 24 hours to give a wet-synthesized HAp/$IP_6$ powder.

<Preparation of Cement>

Using each of the thus wet-synthesized HAp/$IP_6$ powders, a cement specimen was prepared. In cement preparation, 70-120 µl of purified water was added to 0.2 g of each powder (the solid/liquid ratio (powder/kneading liquid) being 1/0.35-1/0.60) to mix them using a rubber spatula, and the mixture was packed in a mold (ø5 mm) and uniaxially pressed at a molding pressure of 2 kN. The thus-prepared cement specimen was dried in the air for 24 hours. The cement specimen had a diameter of 4.5-5 mm, a height of 6-8 mm and a weight of 0.2 g.

<Mechanical Characteristic Evaluation of Cement>

The mechanical characteristic evaluation of cement specimen was always made in compression strength testing. The testing machine used was Shimadzu Corporation's Autograph AGS-J. The measurement conditions were as follows:

| | |
|---|---|
| Cross head speed: | 0.5 mm · s$^{-1}$; |
| Load set at: | 5 kN; |
| Auto Stop: | ON. |

The cement pieces prepared using the respective materials for cement as prepared under the conditions shown in Table 1 were subjected to compression strength measurement. The results are shown in Table 1.

TABLE 1

| Synthesis temperature (° C.) | Rate of stirring (rpm) | Reagent concentration (M) Ca(OH)$_2$ | Reagent concentration (M) H$_3$PO$_4$ | pH adjusting agent Concentration | pH adjusting agent | Rate of dropping of phosphoric acid (ml/min) | Ca/P ratio in HAp | Ca/P ratio in HAp/$IP_6$ |
|---|---|---|---|---|---|---|---|---|
| 37 | 400 | 0.5 | 0.3 | 0.25 | NH$_4$OH | 17 | 1.68 | 1.65 |
| 50 | 400 | 0.5 | 0.3 | 0.25 | NH$_4$OH | 17 | 1.72 | 1.7 |
| 70 | 400 | 0.5 | 0.3 | 0.25 | NH$_4$OH | 17 | 1.77 | 1.74 |
| 37 | 200 | 0.5 | 0.3 | 0.25 | NH$_4$OH | 17 | 1.67 | 1.63 |
| 37 | 400 | 0.5 | 0.3 | 0.25 | NH$_4$OH | 17 | 1.67 | 1.65 |
| 37 | 800 | 0.5 | 0.3 | 0.25 | NH$_4$OH | 17 | 1.69 | 1.66 |
| 37 | 400 | 0.1 | 0.06 | 0.25 | NH$_4$OH | 17 | — | — |
| 37 | 400 | 0.5 | 0.3 | 0.25 | NH$_4$OH | 17 | 1.67 | 1.65 |
| 37 | 400 | 1 | 0.6 | 0.25 | NH$_4$OH | 17 | 1.63 | 1.64 |
| 37 | 400 | 2 | 1.2 | 0.25 | NH$_4$OH | 17 | 1.67 | 1.66 |
| 37 | 400 | 0.5 | 0.3 | 0.25 | NH$_4$OH | 17 | 1.67 | 1.65 |
| 37 | 400 | 0.5 | 0.3 | 1.5M | NaOH | 17 | 1.69 | 1.67 |
| 37 | 400 | 0.5 | 0.3 | 1.5M | KOH | 17 | 1.64 | 1.64 |
| 37 | 400 | 0.5 | 0.3 | 0.25 | NH$_4$OH | 17 | — | — |
| 37 | 400 | 0.5 | 0.3 | 0.25 | NH$_4$OH | 4.2 | — | — |

| Synthesis temperature (° C.) | Median diameter (µm) | Compression strength (MPa) Solid/liquid ratio (powder/kneading liquid) 1/0.35 | 1/0.40 | 1/0.45 | 1/0.50 | 1/0.55 | 1/0.60 |
|---|---|---|---|---|---|---|---|
| 37 | 10.4 | 16.2 ± 2.2 | 10.1 ± 1.2 | 11.6 ± 2.9 | 9.9 ± 1.7 | 7.3 ± 1.1 | 6.7 ± 2.2 |
| 50 | 11.3 | 14.5 ± 0.5 | 10.5 ± 0.8 | 11.8 ± 1.4 | 9.0 ± 1.0 | 7.0 ± 2.9 | 5.0 ± 1.0 |
| 70 | 10.6 | 14.4 ± 2.8 | 8.3 ± 2.5 | 9.1 ± 1.8 | 6.7 ± 0.5 | 3.8 ± 1.7 | 4.7 ± 3.6 |
| 37 | 10.6 | 19.1 ± 0.2 | 15.6 ± 2.0 | 11.8 ± 3.9 | 8.1 ± 3.4 | 8.9 ± 2.6 | 5.4 ± 1.9 |
| 37 | 13.4 | 16.2 ± 1.1 | 13.1 ± 1.8 | 11.4 ± 1.4 | 9.9 ± 1.8 | 9.2 ± 1.4 | 6.6 ± 2.0 |
| 37 | 14.4 | 18.9 ± 2.2 | 12.9 ± 2.2 | 10.7 ± 2.0 | 7.4 ± 2.0 | 6.5 ± 0.9 | 5.3 ± 0.9 |
| 37 | 17.0 | 17.4 ± 1.0 | 14.4 ± 3.4 | 10.6 ± 0.6 | 12.0 ± 3.3 | 6.1 ± 1.9 | 4.5 ± 1.4 |
| 37 | 13.4 | 16.2 ± 1.2 | 13.1 ± 1.8 | 11.4 ± 1.4 | 9.9 ± 1.8 | 9.2 ± 1.4 | 6.6 ± 2.0 |
| 37 | 12.5 | 18.1 ± 2.6 | 14.7 ± 1.3 | 9.9 ± 1.5 | 8.2 ± 2.8 | 7.9 ± 0.4 | 6.4 ± 1.4 |
| 37 | 7.5 | 17.3 ± 2.8 | 16.3 ± 1.7 | 11.7 ± 1.1 | 11.0 ± 1.1 | 6.1 ± 0.9 | 4.3 ± 1.8 |
| 37 | 12.6 | 17.5 ± 2.1 | 12.7 ± 2.6 | 12.4 ± 4.4 | 9.6 ± 1.6 | 8.1 ± 1.9 | 6.7 ± 1.1 |
| 37 | 15.1 | 16.4 ± 3.6 | 9.6 ± 2.6 | 12.3 ± 1.9 | 7.4 ± 4.6 | 7.5 ± 3.1 | 6.5 ± 1.6 |
| 37 | 12.0 | 17.1 ± 1.1 | 11.5 ± 4.9 | 15.8 ± 2.6 | 10.7 ± 1.2 | 7.8 ± 0.8 | 6.3 ± 0.9 |
| 37 | 13.4 | 16.2 ± 1.2 | 13.1 ± 1.8 | 11.4 ± 1.4 | 9.9 ± 1.8 | 9.2 ± 1.4 | 6.6 ± 2.0 |
| 37 | 12.7 | 15.6 ± 1.1 | 11.7 ± 1.2 | 6.9 ± 0.9 | 6.7 ± 2.1 | 6.2 ± 1.3 | 4.0 ± 2.2 |

Based on the results shown in Table 1, those experimental parameters which gave high levels of compression strength at a solid/liquid ratio of 1/0.35 were selected for the subsequent experiment examples. Specifically, the wet synthesis conditions for HAp as selected were as follows: synthesis temperature 37° C., rate of stirring 200 rpm, reagent concentrations: calcium hydroxide concentration 0.5 M and phosphoric acid concentration 0.3 M, pH adjusting agent 25% NH$_4$OH, and rate of dropping of phosphoric acid 17 ml/min.

Drying Method in Wet Synthesis and Changes in Powder Characteristics Upon Calcination Example 2

Freeze Dried HAp/IP$_6$ Powder Preparation

A "freeze dried HAp/IP$_6$ powder" was prepared using the synthesis conditions obtained in Example 1.

Using the freeze dried HAp/IP$_6$ powder obtained, cement specimens were prepared in the same manner as in Example 1 and measured for compression strength. The results are shown in Table 2.

<Median Diameter and Particle Size Distribution Measurements>

The median diameter and particle size distribution of the freeze dried HAp/IP$_6$ powder were measured using the laser diffraction/scattering particle size distribution measurement apparatus LA-300 (product of Horiba Ltd.). The sample was dispersed in purified water and the measurements were made using a flow cell. The median diameter of the freeze dried HAp/IP$_6$ powder is shown in Table 2, and the results of the particle size distribution measurement are shown in FIG. 1.

<Specific Surface Area Measurement>

The specific surface area (SSA) of the freeze dried HAp powder was measured by the BET method using the Micromeritics automated surface area measuring apparatus FlowSorb III 2305 (product of Shimadzu Corporation). The sample size was 0.2 g and liquefied nitrogen was used as the coolant. The corrected value of the amount at saturated adsorption was calculated using the following formula.

$$SSA = (273.2/\text{atmospheric temperature (° C.)}) \times \text{atmospheric pressure (mm Hg)}/760) \times ((6.023 \times 10^{23} \times 16.2 \times 10^{-23})(22.414 \times 10)) \times (1 - (\text{nitrogen percentage (\%)} \times \text{atmospheric pressure (mm Hg)})/775)$$

The amount of gas adsorbed on the powder upon cooling of the sample with the coolant (adsorption data) and the amount of gas released from the powder upon taking out of the sample from the coolant (desorption data) were measured. The desorption data was employed as the experimental value. The results of the specific surface area measurement of the freeze dried HAp powder are shown in Table 2 and FIG. 2.

<Crystal Phase Identification by X Ray Diffractometry (XRD)>

Figure 3:
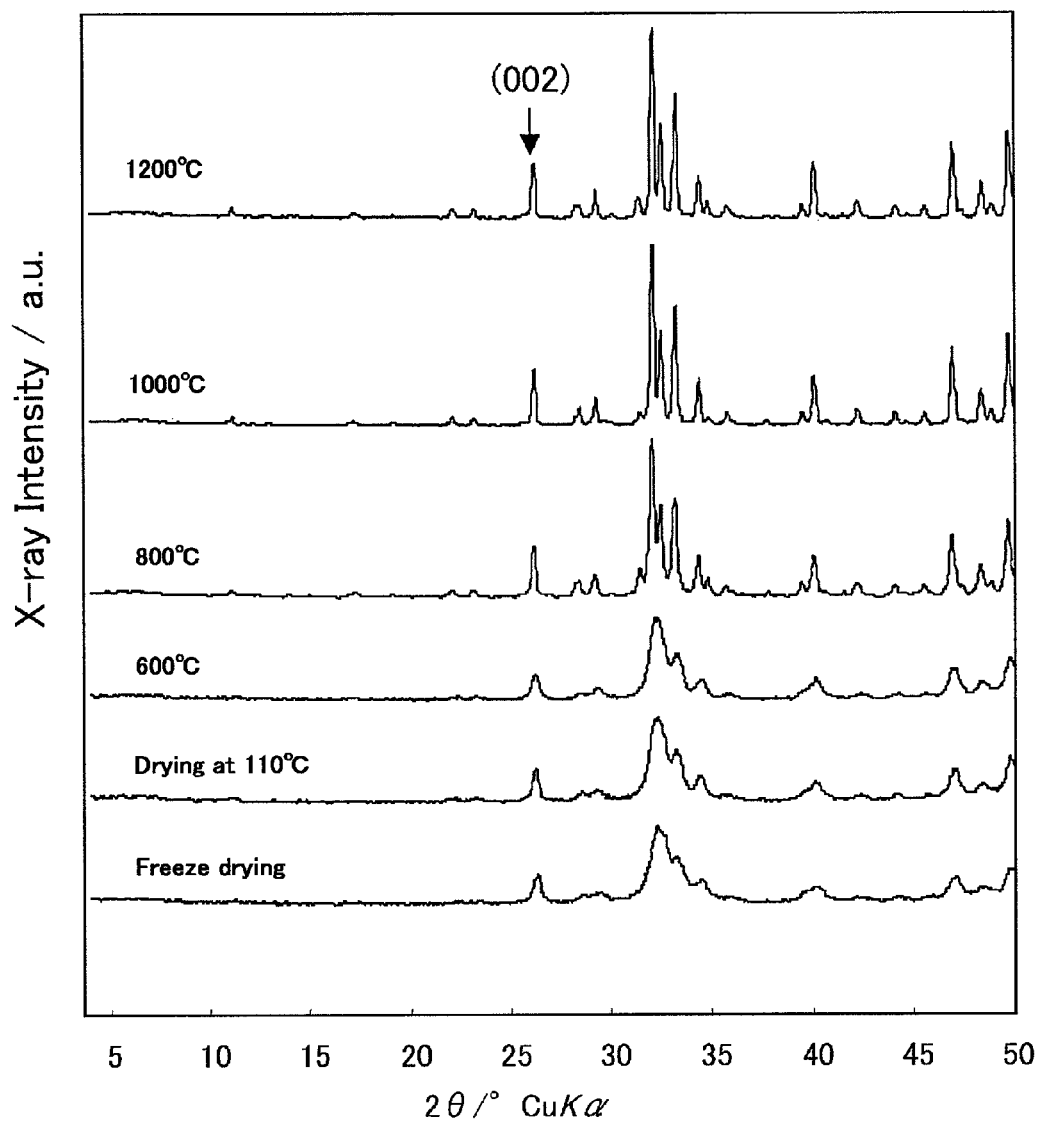
FIG. 3 shows the X ray diffraction patterns of the wet-synthesized HAp/IP$_6$ powder, the HAp/IP$_6$ powder dried at 110° C., and the calcined HAp/IP$_6$ powder as recorded by X ray diffractometry (XRD).

The freeze dried HAp/IP$_6$ powder was identified by X ray diffractometry using a powder X ray diffractometer. The measurement was carried out using Rigaku MiniFlex (product of Rigaku Corporation) at an applied voltage of 30 kV and a tube current of 15 mA. The crystal phases before and after surface modification were identified using JCPDS cards. The X ray diffraction patterns obtained are shown in FIG. 3. The (002) plane half width is shown in Table 2.

Example 3

HAp/IP$_6$ Powder Preparation by Drying at 110° C.

The wet synthesis was carried out in the same manner as in Example 2 and, after maturation, the HAp slurry was recovered by suction filtration, then suspended in 300 cm$^3$ of acetone and again recovered by suction filtration. The recovered HAp slurry was air-dried until disappearance of the acetone and then dried in a dryer set at 110° C. for 2 days. Otherwise the same procedure as in Example 2 was followed to give a "HAp/IP$_6$ powder dried at 110° C.".

Figure 2:
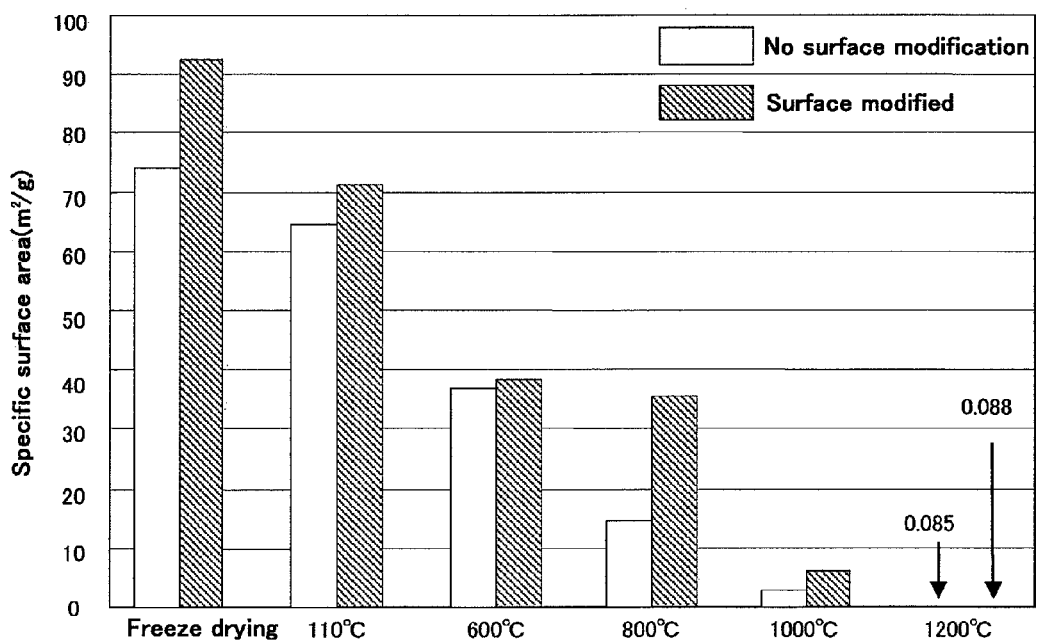
FIG. 2 shows the results of specific surface area measurements of the wet-synthesized HAp/IP$_6$ powder, the HAp/IP$_6$ powder dried at 110° C., and the calcined HAp/IP$_6$ powder.

For the HAp/IP$_6$ powder obtained by drying at 110° C., the median diameter is shown in Table 2, the results of the particle size distribution measurement are shown in FIG. 1, the results of the specific surface area measurement are shown in Table 2 and FIG. 2, the X ray diffraction pattern is shown in FIG. 3, and the half width is shown in Table 2. Using the HAp/IP$_6$ powder obtained by drying at 110° C., cement specimens were prepared in the same manner as in Example 1 and measured for compression strength; the results are shown in Table 2.

Comparative Examples 1-4

Calcined HAp/IP$_6$ Powder Preparation

The HAp slurry recovered in the same manner as in Example 3 was air-dried until disappearance of the acetone and then calcined at various temperatures (600° C., 800° C., 1,000° C., 1,200° C.) using a box-type electric furnace (product of Koyo Thermo Systems). Otherwise the same procedure as in Example 2 was followed to give "calcined HAp/IP$_6$ powders (600° C., 800° C., 1,000° C., 1,200° C.)".

For each of the calcined HAp/IP$_6$ powders obtained, the median diameter is shown in Table 2, the results of the particle size distribution measurement are shown in FIG. 1, the results of the specific surface area measurement are shown in Table 2 and FIG. 2, the X ray diffraction pattern is shown in FIG. 3, and the half width is shown in Table 2. Using the calcined HAp/IP$_6$ powders obtained, cement specimens were prepared in the same manner as in Example 1 and measured for compression strength; the results are shown in Table 2.

TABLE 2

| Sample name | Drying/ calcination conditions | Specific surface area (m$^2$/g) | (002) plane half width (°) | Median diameter (μm) | Compression strength (MPa) Solid/liquid ratio (powder/kneading liquid) | | | | | |
|---|---|---|---|---|---|---|---|---|---|---|
| | | | | | 1/0.35 | 1/0.40 | 1/0.45 | 1/0.50 | 1/0.55 | 1/0.60 |
| Example 2 | Freeze drying | 92.5 | 0.396 | 11.7 | 19.1 ± 0.2 | 15.6 ± 2.0 | 11.8 ± 3.9 | 8.1 ± 3.4 | 8.9 ± 2.6 | 5.4 ± 1.9 |
| Example 3 | 110° C. | 71.7 | 0.345 | 15.8 | 16.6 ± 0.7 | 13.3 ± 1.6 | 11.4 ± 1.7 | 7.3 ± 2.6 | 5.6 ± 1.1 | — |
| Comparative Example 1 | 600° C. | 38.8 | 0.442 | 22.2 | 5.6 ± 0.2 | 7.7 ± 1.0 | 9.7 ± 0.1 | 4.6 ± 1.5 | 8.9 ± 2.6 | — |
| Comparative Example 2 | 800° C. | 35.6 | 0.278 | 15.0 | 6.6 ± 0.3 | 6.0 ± 0.8 | 6.4 ± 0.9 | 3.5 ± 0.7 | 2.7 ± 0.1 | — |

TABLE 2-continued

| Sample name | Drying/ calcination conditions | Specific surface area ($m^2/g$) | (002) plane half width (°) | Median diameter (μm) | Compression strength (MPa) Solid/liquid ratio (powder/kneading liquid) | | | | | |
|---|---|---|---|---|---|---|---|---|---|---|
| | | | | | 1/0.35 | 1/0.40 | 1/0.45 | 1/0.50 | 1/0.55 | 1/0.60 |
| Comparative Example 3 | 1,000° C. | 6.0 | 0.212 | 24.8 | 4.5 ± 0.8 | — | — | — | — | — |
| Comparative Example 4 | 1,200° C. | 0.1 | 0.215 | 27.0 | — | — | — | — | — | — |

Raw Material Size Reduction by Ball Mill Pulverization

Example 4

Preparation of a Dry-Pulverized HAp/IP$_6$ Powder

A wet-synthesized HAp powder obtained in the same manner as in Example 2 was pulverized in a P-6 satellite ball mill (product of Fritsch) under the following conditions.

A 10.0 g portion of the wet-synthesized HAp powder prepared in the same manner as in Example 2 was placed, together with 50 zirconia balls having a diameter of 10 mm, in a zirconia-made pot and dry-pulverized at a rotation rate of 300 rpm for 5 minutes. After pulverization, the sample was recovered by rinsing out of the vessel using purified water and the pulverized HAp slurry was recovered by suction filtration. The slurry recovered was frozen overnight at −80° C. and then dried for 24 hours using the freeze dryer Free Zone (trademark) (product of Labconco) to give a dry-pulverized HAp powder.

Figure 4:
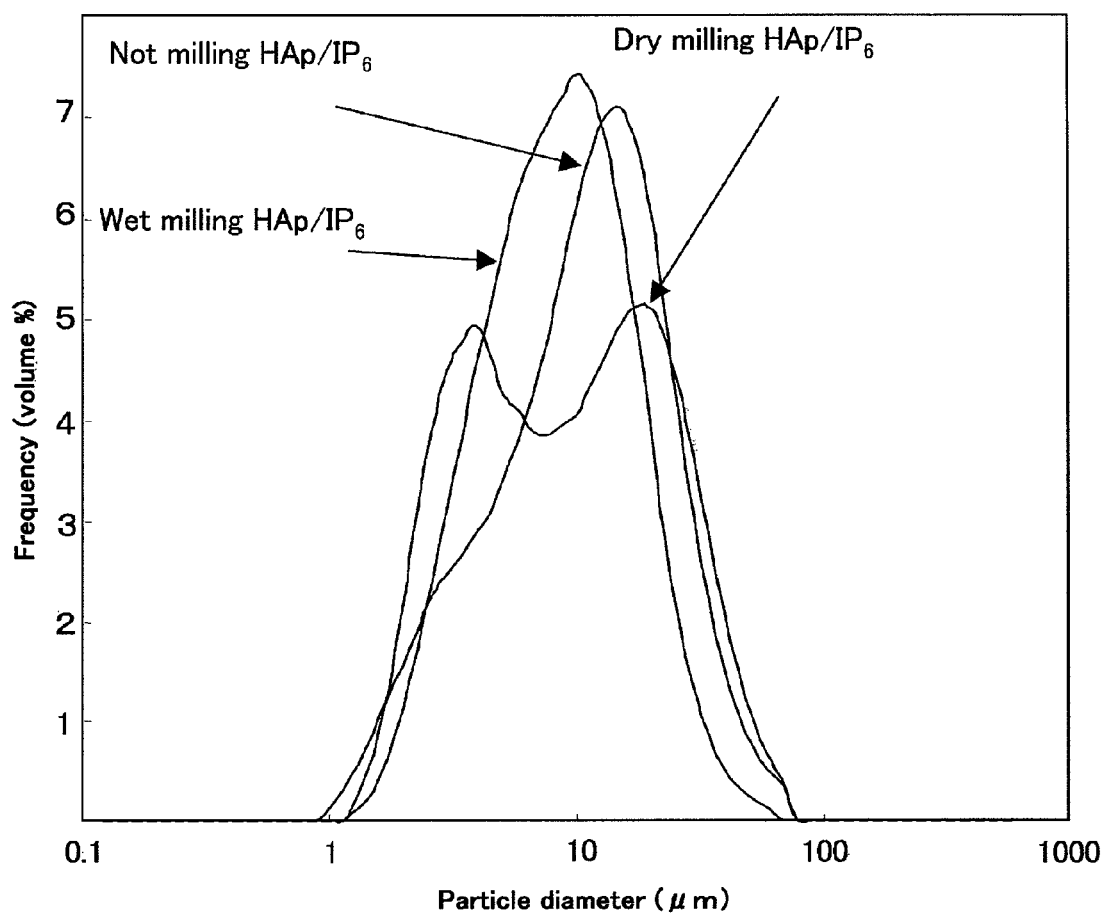
FIG. 4 shows the results of particle size distribution measurements of a HAp/IP$_6$ powder, a dry-pulverized HAp/IP$_6$ powder, and a wet-pulverized HAp/IP$_6$ powder.

Otherwise the same procedure as in Example 2 was followed to give a "dry-pulverized HAp/IP$_6$ powder". For the dry-pulverized HAp/IP$_6$ powder obtained, the results of the particle size distribution measurement are shown in FIG. 4, and the median diameter, specific surface area and half width are shown in Table 3. Using the dry-pulverized HAp/IP$_6$ powder obtained, cement specimens were prepared in the same manner as in Example 1 except that the solid/liquid ratio (powder/kneading liquid) was varied from 1/0.31 to 1/0.60; the cement specimens were measured for compression strength; the results are shown in Table 3.

Example 5

Preparation of a Wet-Pulverized HAp/IP$_6$ Powder

A 10.0 g portion of a wet-synthesized HAp powder prepared in the same manner as in Example 2 was placed, together with 50 zirconia balls having a diameter of 10 mm and 40 ml of purified water, in a zirconia-made pot and wet-pulverized at a rotation rate of 300 rpm for 5 minutes. Thereafter, otherwise the same procedure as in Example 4 was followed to give a "wet-pulverized HAp/IP$_6$ powder". For the wet-pulverized HAp/IP$_6$ powder obtained, the results of the particle size distribution measurement are shown in FIG. 4, and the median diameter, specific surface area and half width are shown in Table 3. Using the wet-pulverized HAp/IP$_6$ powder obtained, cement specimens were prepared in the same manner as in Example 1 except that the solid/liquid ratio (powder/kneading liquid) was varied from 1/0.31 to 1/0.60; the cement specimens were measured for compression strength; the results are shown in Table 3.

TABLE 3

| Sample name | Pulverizing method | Specific surface area ($m^2/g$) | (002) plane half width (°) | Median diameter (μm) | Compression strength (MPa) Solid/liquid ratio (powder/kneading liquid) | | |
|---|---|---|---|---|---|---|---|
| | | | | | 1/0.31 | 1/0.32 | 1/0.33 |
| Example 4 | Dry pulverization | 94.2 | 0.417 | 8.7 | 12.5 ± 1.8 | 11.3 ± 0.9 | 10.1 ± 1.1 |
| Example 5 | Wet pulverization | 98.5 | 0.383 | 7.9 | 16.6 ± 3.8 | 17.3 ± 5.1 | 17.0 ± 2.8 |

| Sample name | Compression strength (MPa) Solid/liquid ratio (powder/kneading liquid) | | | | | |
|---|---|---|---|---|---|---|
| | 1/0.35 | 1/0.40 | 1/0.45 | 1/0.50 | 1/0.55 | 1/0.60 |
| Example 4 | 17.2 ± 1.0 | 11.8 ± 0.5 | 8.7 ± 0.1 | 4.5 ± 1.0 | 2.7 ± 0.4 | — |
| Example 5 | 25.3 ± 2.3 | 15.3 ± 0.8 | 8.2 ± 2.2 | 9.3 ± 0.8 | 8.3 ± 1.1 | 5.8 ± 1.3 |

Investigations Concerning the Chelating Agent and the Method of Addition Thereof

Comparative Example 5

Preparation of a HAp/EDTA Powder

A 10.0 g portion of a wet-synthesized HAp powder prepared in the same manner as in Example 2 was suspended in 200 cm$^3$ of an EDTA solution having a concentration of 1,000 ppm, and the suspension was stirred at a stirring rate of 400 rpm at 37° C. for 5 hours. Otherwise the same procedure as in Example 2 was followed to give a "HAp/EDTA powder".

For the HAp/EDTA powder obtained, the median diameter, specific surface area and half width are shown in Table 4. Using the HAp/EDTA powder, cement specimens were prepared in the same manner as in Example 1 and measured for compression strength; the results are shown in Table 4.

Examples 6 and 7

The Case of Changing the Chelating Agent Concentration

A wet-synthesized HAp powder was prepared following the same procedure as in Example 2, 10.0 g portions thereof were each suspended in 200 cm$^3$ of an aqueous IP$_6$ solution having a concentration of 5,000 ppm or 10,000 ppm, and each suspension was stirred at a stirring rate of 400 rpm at 37° C. for 5 hours. Otherwise the same procedure as in Example 2 was followed to give a "HAp/5000 IP$_6$ powder" and a "HAp/10000 IP$_6$ powder", respectively. For each of the powders obtained, the median diameter, specific surface area and half width are shown in Table 4. Using each powder, cement specimens were prepared in the same manner as in Example 1 and measured for compression strength; the results are shown in Table 4.

<The Case of Changing the Timing of Addition of IP$_6$>

Three HAp/IP$_6$ powders were synthesized by adding IP$_6$ while the timing of addition thereof was varied in three ways (timing 1 to timing 3).

Example 9

The Case of Addition of IP$_6$ in the Step of Synthesis (Timing 3)

To 500 cm$^3$ of a calcium hydroxide suspension with a concentration of 0.5 M were added dropwise 500 cm$^3$ of an aqueous phosphoric acid solution with a concentration of 0.3 M and 500 cm$^3$ of an aqueous IP$_6$ solution with a concentration of 1,000 ppm at a rate of 17 cm$^3$/minute. On that occasion, the rate of stirring was maintained at 200 rpm and the solution temperature at 37° C., and the pH of the solution was adjusted to 10<pH<11 with a 25% NH$_4$OH solution. After dropping of phosphoric acid, the mixture was further stirred for 1 hour and then allowed to stand in an incubator set at 37° C. for 24 hours for maturation. After maturation, the HAp slurry was recovered by suction filtration and frozen overnight at −80° C. The frozen HAp/IP$_6$ slurry was dried for 24 hours using the freeze dryer Free Zone (trademark) (product of Labconco) to give a "wet-method HAp/IP$_6$ powder (timing 3)". For the wet-method HAp/IP$_6$ powder (timing 3), the median diameter, specific surface area and half width are shown in Table 4. Using the wet-method HAp/IP$_6$ powder (timing 3), cement specimens were prepared in the same manner as in Example 1 and measured for compression strength; the results are shown in Table 4.

TABLE 4

| Sample name | Chelating agent Species | Concentration (ppm) | Timing | Specific surface area (m$^2$/g) | (002) plane half width (°) | Median diameter (μm) | Compression strength (MPa) Solid/liquid ratio (powder/kneading liquid) | | | | | |
|---|---|---|---|---|---|---|---|---|---|---|---|---|
| | | | | | | | 1/0.35 | 1/0.40 | 1/0.45 | 1/0.50 | 1/0.55 | 1/0.60 |
| Comparative Example 5 | EDTA | 1,000 | 1 | 40.5 | 0.524 | 9.4 | 13.8 ± 1.1 | 11.4 ± 2.7 | 8.8 ± 1.5 | 6.9 ± 2.2 | 5.9 ± 2.0 | 4.2 ± 0.7 |
| Example 6 | IP$_6$ | 5,000 | 1 | 98.8 | 0.359 | 18.1 | 18.0 ± 2.3 | 9.9 ± 3.1 | 9.9 ± 6.1 | — | — | — |
| Example 7 | IP$_6$ | 10,000 | 1 | 95.6 | 0.349 | 17.6 | 14.1 ± 3.2 | 7.1 ± 1.9 | — | — | — | — |
| Example 8 | IP$_6$ | 1,000 | 2 | 95.9 | 0.360 | 11.2 | 16.2 ± 1.6 | 9.3 ± 1.3 | 9.4 ± 2.9 | 7.6 ± 1.9 | 5.5 ± 1.7 | 5.8 ± 1.6 |
| Example 9 | IP$_6$ | 1,000 | 3 | 112.0 | 0.384 | 14.7 | 22.4 ± 1.9 | 16.3 ± 1.6 | 11.9 ± 4.6 | 10.5 ± 1.9 | 8.7 ± 1.2 | 7.4 ± 1.4 |

Timing 1 corresponds to the method described above (Example 2).

Example 8

The Case of Addition of IP$_6$ to HAp in the State of Slurry (Timing 2)

The wet synthesis was carried out in the same manner as in Example 2 and, after maturation, the HAp slurry was recovered by suction filtration. The slurry recovered was suspended, without drying, in 500 cm$^3$ of an aqueous IP$_6$ solution having a concentration of 1,000 ppm, and the suspension was stirred at a rate of stirring of 400 rpm at 37° C. for 5 hours, followed by suction filtration. The slurry obtained was washed with purified water and then frozen overnight at −80° C. The frozen slurry was dried for 24 hours using the freeze dryer Free Zone (trademark) (product of Labconco) to give a "wet-method HAp/IP$_6$ powder (timing 2)". For the wet-method HAp/IP$_6$ powder (timing 2) obtained, the median diameter, specific surface area and half width are shown in Table 4. Using the wet-method HAp/IP$_6$ powder (timing 2), cement specimens were prepared in the same manner as in Example 1 and measured for compression strength; the results are shown in Table 4.

Comparative Example 6

HAp-100 (hydroxyapatite, product of Taihei Chemical) was classified through a sieve with a sieve opening of 37 μm to give a HAp-100 powder fraction with a median diameter of 18.3 μm (specific surface area 48.2 m$^2$/g). A 2.5 g portion of the thus-obtained classified HAp-100 powder fraction was added to 50 ml of an aqueous IP$_6$ solution (3.0 mM, pH 7.3, 0.15 mmol), and the mixture was shaken for 5 hours. The HAp-100/IP$_6$ was collected by suction filtration and dried under reduced pressure for 24 hours. Water was added to the HAp-100/IP$_6$ thus prepared at a solid/liquid ratio of 1/0.60 (weight ratio) and, after 1 minute of kneading, the mixture was packed in a mold. After hardening, the cement specimen was measured for compression strength; the compression strength was 6.8 MPa.

Example 10

(1) Preparation of a Simulated Body Fluid

To about 700 ml of distilled water were added sodium chloride (7.996 g), sodium hydrogen carbonate (0.350 g), potassium chloride (0.224 g), potassium hydrogen phosphate trihydrate (0.228 g), magnesium chloride hexahydrate (0.305 g), 1 M hydrochloric acid (40 ml), calcium chloride (0.278 g), sodium sulfate (0.071 g) and trishydroxymethylaminomethane (6.057 g), in that order. The solution was adjusted to pH 7.40 using 1 M hydrochloric acid and then the whole amount was made exactly 1,000 ml by adding distilled water.

(2) Immersion Test Using the Simulated In Vivo Body Fluid

The cement specimens prepared in Example 1 were immersed in the simulated body fluid and the compression strength of the cement and the calcium ion or phosphate ion concentration in the simulated body fluid were measured at timed intervals.

The calcium ion or phosphate ion concentration in the simulated body fluid decreased with the lapse of time and, on the 6th day and thereafter, remained at a constant ion concentration level. This result suggests that calcium phosphate precipitated out on the cement and, considering the rates of changes over time in calcium ion and phosphate ion concentrations, the precipitate was presumably HAp.

The compression strength of the cement after 30 days of immersion in the simulated body fluid was measured and found to be 19.1 MPa.

Example 11

Osteoblast-like cells (MC3T3-E1) ($6 \times 10^4$ cells) were seeded in a polystyrene plate and cultivated for 1 day. A Transwell was placed in the polystyrene plate and the cement specimen prepared in Example 1 was placed therein, and cells were counted after 2, 4, 6 and 8 days.

The number of cells increased with time and arrived at a point of saturation after 6 days. This result revealed that the cement according to the present invention has good biocompatibility.

What is claimed is:

1. A material for cement, characterized in that:
   it comprises a calcium salt powder with an inositol phosphate and/or a salt thereof as adsorbed on the surface thereof; and
   the powder has a specific surface area of 60-120 m$^2$/g after adsorption,
   wherein the calcium salt is hydroxyapatite,
   wherein the inositol phosphate is phytic acid (inositol hexaphosphate).

2. The material for cement according to claim 1, wherein the hydroxyapatite powder shows a (002) plane half width of 0.30-0.45° as determined by X ray diffractometry.

3. The material for cement according to claim 1, wherein the powder has a median diameter within the range of 5-20 μm and the content of particles having a diameter of 3-50 μm is not lower than 60% by volume of the whole powder.

4. A method of producing the material for cement according to claim 1, characterized in that it comprises:
   the step of mixing a calcium ion-containing solution adjusted to alkalinity with a phosphate ion-containing solution to produce a precipitate;
   the step of maturing the precipitate-containing system while maintaining the alkalinity to obtain a hydroxyapatite powder;
   the step of recovering the hydroxyapatite powder and drying the same; and
   the step of immersing the dried hydroxyapatite powder in a solution containing phytic acid and/or a salt thereof to cause the phytic acid and/or salt thereof to be adsorbed on the surface of the hydroxyapatite powder.

5. The method of producing the material for cement according to claim 4, wherein the precipitate-containing system is maintained at a temperature of 20-70° C. to obtain the hydroxyapatite powder.

6. The method of producing the material for cement according to claim 4, wherein the step of recovering and drying the hydroxyapatite powder is carried out in the manner of freeze drying or drying by heating at 50-150° C.

7. The method of producing the material for cement according to claim 4 which further comprises the step of pulverizing the dried hydroxyapatite powder.

8. The method of producing the material for cement according to claim 7, wherein the step of pulverizing is carried out in the manner of wet pulverization using a vessel-driven medium mill.

9. The method of producing the material for cement according to claim 1, characterized in that it comprises:
   the step of mixing a calcium ion-containing solution adjusted to alkalinity, a phosphate ion-containing solution and a solution containing phytic acid and/or a salt thereof together to produce a precipitate; and
   the step of maturing the precipitate-containing system while maintaining the alkalinity to obtain a phytic acid-carrying hydroxyapatite powder,
   wherein the powder has a specific surface area of 60-120 m$^2$/g after adsorption.

10. A cement characterized in that it is produced by kneading the material for cement according to claim 1 with an aqueous solvent, followed by hardening.

11. The cement according to claim 10 which has a compression strength, after hardening, of not lower than 14 MPa.

12. The cement according to claim 10, wherein the kneading of the material for cement with the aqueous solvent is carried out with a mixture ratio by weight (solid to liquid ratio) between 1/0.31 and 1/0.45.

* * * * *